United States Patent [19]

Nogami et al.

[11] Patent Number: 5,661,558
[45] Date of Patent: Aug. 26, 1997

[54] OPTICAL DETECTOR FOR FLOWING SAMPLE AND OPTICAL DETECTION METHOD FOR FLOWING SAMPLE

[75] Inventors: Taro Nogami, Hitachinaka; Yoshiaki Yamada, Ishioka; Synichi Mathuura, Toukai-mura, all of Japan

[73] Assignee: Hitachi, Ltd., Tokyo, Japan

[21] Appl. No.: 492,879

[22] Filed: Jun. 20, 1995

[30] Foreign Application Priority Data

Jun. 30, 1994 [JP] Japan ................................. 6-148976

[51] Int. Cl.$^6$ ................................................. G01N 21/85
[52] U.S. Cl. ........................... 356/319; 356/410; 356/411
[58] Field of Search ............................... 356/319, 410, 356/411

[56] References Cited

U.S. PATENT DOCUMENTS

| | | | |
|---|---|---|---|
| 3,614,242 | 10/1971 | Hrdina | 356/410 |
| 4,014,612 | 3/1977 | Atwood et al. | 356/419 X |
| 4,367,041 | 1/1983 | Webb, Jr. et al. | 356/72 |
| 5,153,679 | 10/1992 | Gilby | 356/410 X |

FOREIGN PATENT DOCUMENTS

| | | | |
|---|---|---|---|
| 60-224031 | 1/1985 | Japan | 356/411 |
| 62-113033 | 5/1987 | Japan | 356/319 |
| 1515632 | 6/1978 | United Kingdom . | |

OTHER PUBLICATIONS

Nordal et al "Visible–light spectroscopy by photothermal radiometry using incoherent source," Appl. Phys. Lett. 38 (7) (1 Apr. 1981), pp. 486–488.

*Primary Examiner*—Vincent P. McGraw
*Attorney, Agent, or Firm*—Kenyon & Kenyon

[57] ABSTRACT

An optical detector for flowing sample comprises a light condenser for condensing a diverging monochrome light, a flow cell arranged in the course of convergence of the converged light beam, and a sample-side detector for receiving a sample-side light. Such a construction makes it possible to correct delicate changes of the light axis due to intensity, position, temperature changes of the light source, density change of the flowing liquid, and any change of other causes effectively for stable sample analysis without difficult optical adjustment.

12 Claims, 2 Drawing Sheets

OPTICAL DETECTOR FOR FLOWING SAMPLE AND OPTICAL DETECTION METHOD FOR FLOWING SAMPLE

BACKGROUND OF THE INVENTION

1. Field of the Invention

The present invention relates to an optical detector for flowing sample and an optical detection method for flowing sample.

2. Description of the Related Art

In a general prior art for analyzing a sample an optical detector for flowing sample is frequently used. The optical detector for flowing sample irradiated a light from a light source to the sample made to flow in a light transmitting flow path before detecting the light having passed the sample. The sample then is analyzed on the basis of results of the detection.

In the prior art for leading a light from a light source to a light transmitting flow path, a slit is arranged before the light transmitting flow path, the light from the light source is converged at the slit before coming in the light transmitting flow path, and after that the light is irradiated to the sample.

As the light is converged before the light transmitting flow path in that way, the light is minimized in the cross-sectional area when it passes the slit before passing the light transmitting flow path while being diverging. The prior art is disadvantageous in that parts or all of the light beam are reflected or absorbed by the inside walls of the light transmitting flow path or the slit.

Another known prior art has a light transmitting flow path formed so as to track along a diverging light beam. The prior art can solve the disadvantage that the light beam is reflected or absorbed by the inside walls of the light transmitting flow path. However, the prior art cannot prevent the light beam from being reflected or absorbed by the slit still. The prior art also has such a disadvantage that since diameter of the flow path is different at positions, the density distribution of the liquid pressure is dispersed. This results in deviation of the track of the light beam.

In view of the foregoing, it is an object of the present invention to provide an optical detector and detection method for flowing sample that can solve the problems of difficulties in the light path.

SUMMARY OF THE INVENTION

Briefly, the foregoing object is accomplished in accordance with aspects of the present invention by the construction that a light from a light source is converged in a light transmitting flow path.

Preferably, the optical detector for flowing sample comprises a light source, a spectroscope for separating a light emitted from the light source, a detector for detecting a light led out of the spectroscope, a light transmitting flow path (flow cell) positioned in a light path between the detector and the spectroscope, wherein at least a slit and a light condenser for condensing a dispersed light having passed the slit are arranged in that order between the spectroscope and the flow cell in the light path.

Further preferably, the optical detector for flowing sample provides the feature that the light transmitting flow path (flow cell) is positioned so that a direction of the light path coincides with a sample flowing direction of the flow cell and the flow cell and the light condenser are arranged so that a focus of the light condenser is positioned at a center of or near the center of a sample flow path of the flow cell.

Depending on situation, the flow cell or the light condenser is arranged so that the focus of the light condenser is positioned at an end of or near the end of the flow cell in the light path direction.

Further, a light beam splitter is arranged in the course of convergence of the light condenser to split the light beam to the sample side and reference side.

Since the optical detector for flowing sample is constructed as described above, the light beam can enter the light transmitting flow path as being converged and can be focused in the light transmitting flow path.

Since the focus is put within the light transmitting flow path, little light beam is cut by the inside walls even if the light beam passes over the focus position and diverges.

Since the light condenser can have the focus at a desired position in the sample flow path as described in the preferable construction, the optical system can be set depending on cause of measurement error. As an example, the focus should be ordinarily put at the center of the sample flow path to which most of the light beam enters the light transmitting flow path (flow cell). If the optical axis in the flow cell is changed too much by density change of the liquid flowing in the flow cell, the focus should be set to the sample-side detector.

The light beam splitter for splitting the light beam can be arranged on the sample and reference sides in the course of convergence of the light converging means to feed the light beam of virtually the same condition to the both detectors.

The present invention has the sample-side and object-side optical systems arranged to have as the same conditions as possible to make delicate optical axis adjustment unnecessary. The present invention also allows easy corrections of change of the light source position by the object-side signal, slight deviation of the optical axis, and other changes that have been ordinarily difficult to correct.

DETAILED DESCRIPTION OF THE PREFERRED EMBODIMENTS

The following describes in detail an embodiment according to the present invention by reference to the accompanying drawings.

Figure 1:
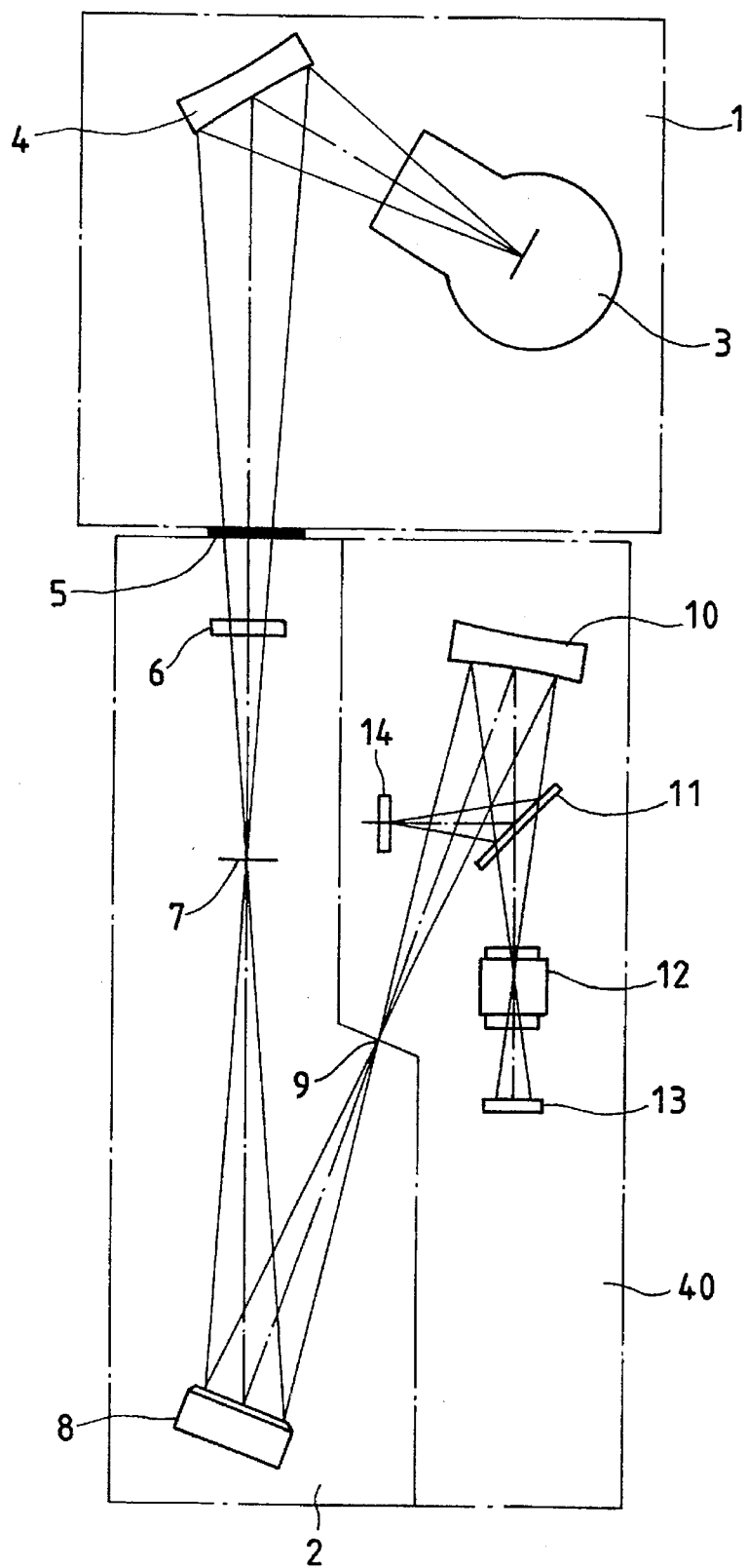
FIG. 1 is an outline illustrating an embodiment according to the present invention.

FIG. 1 depicts an outline illustrating an optical system of the optical detector for flow sample according to the present invention. The detector of the embodiment comprises a light source chamber 1, a spectroscope chamber 2, and a detector chamber 40. A light is emitted by a deuterium lamp 3. The emitted light is condensed by a light condensing mirror 4. The condensed light enters the spectroscope chamber 2 from a quartz window 5. The light then enters the spectroscope from a light incoming slit 7 through a cut filter 6. The light is dispersed for each wavelength by a concave diffraction grating 8. The light of a single wavelength enters the detector chamber 40 from a light outgoing slit 9. After that, the monochromatic light is converged again by a light recondensing mirror 10 to direct toward a flow cell 12. A beam splitter 11 is put in a light path in which the light is converged. The beam splitter 11 directs parts of the monochromatic light toward an object-side detector 14. The light beam directed to the flow cell 12 is converted within the flow cell 12 before entering a sample-side detector 13. Since a distance from the light recondensing mirror 10 to the flow cell 12 is shorter than the one from the light outgoing slit 9 to the light recondensing mirror 10, a contracted image of the light outgoing slit 9 is formed in the flow cell 12.

Since the detector chamber 40 does not have after the beam splitter 11 such a very narrow opening as the slits of the spectroscope chamber 2, quantities of the lights entering the sample-side detector 13 and the object-side detector 14 are made equal at a high degree. The light quantities therefore can be precisely corrected by comparing outputs of the sample-side detector 13 and the object-side detector 14.

Figure 2:
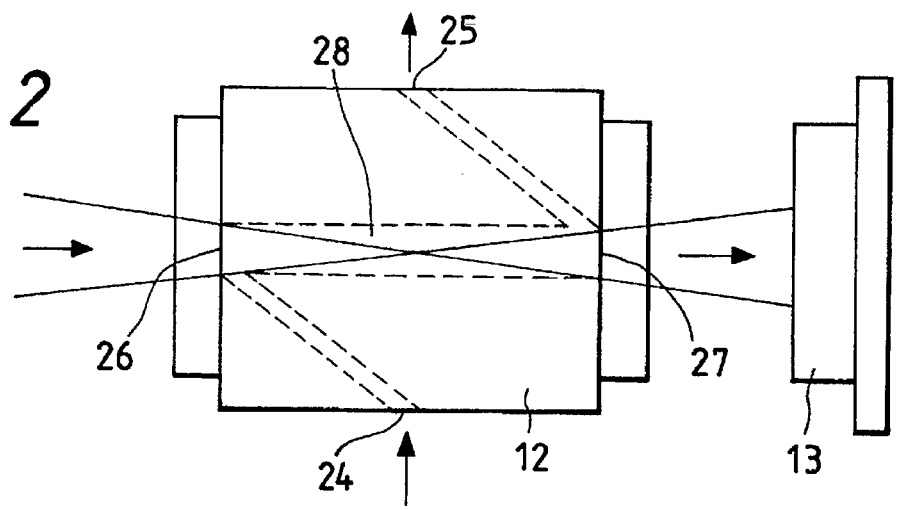
FIG. 2 is a cross-sectioned view illustrating an example of relationship between a position of convergence of light beam and that of the flow cell used in the embodiment of FIG. 1.

FIG. 2 depicts a cross-sectioned view illustrating a relationship between the flow cell 12 used in the embodiment and the sampleside light beam.

The flow cell 12 is formed of quartz, is shaped approximately cylindrical, and has a light transmitting flow path 28 along an axis thereof. The light transmitting flow path 28 is a light path, having a light incoming port 26 and a light outgoing port 27. The light transmitting flow path 28 also is a flow path that allows a liquid to flow in the same direction as the optical axis in the course that the liquid enters a liquid entrance 24 before coming out of a liquid exit 25. The flow path is also used to measure light absorption of the sample by its components. Many prior arts have an outgoing slit of a spectroscope just before an end of a light incoming side of a flow cell, and the light having passed its narrow opening passes a flow path in the flow cell while being broadened. On the other hand, the embodiment shown in FIG. 2 has the light beam converged at a point near a center of the light transmitting flow path 28. This makes it possible to reduce parts of the light beam cut by inside walls of the light transmitting flow path 28 even at portions near an end of any of the light incoming and outgoing sides. This feature is important in that change of the signal can be caused less by little change of the optical axis, being beyond the significance of less loss of the light energy.

Figure 3:
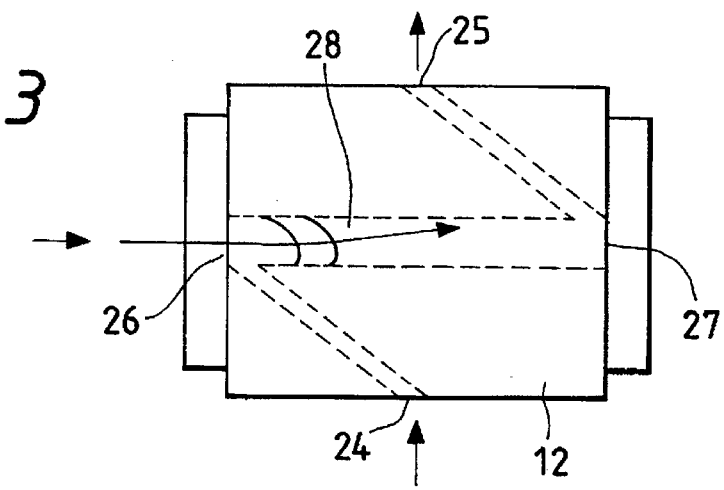
FIG. 3 is a cross-sectioned view illustrating another example of relationship between a position of convergence of light beam and that of the flow cell used in the embodiment of FIG. 1.

FIG. 3 depicts a view illustrating deviation of the light axis in the flow cell 12 by change of composition of the liquid. If density of the liquid entering the light transmitting flow path 28 from a lower side of the end of the light transmitting flow path 28 is changed with oblique rise of the liquid entering from the liquid entrance, an interface of the density does not always become at right angles to the axis of the light transmitting flow path 28, but there may appear oblique interfaces, particularly near the ends, as shown in the figure. The oblique interfaces cause the light to refract, deviating the light axis. The change of the signal due to the light axis deviation is large as the light beam is broadened near the end of the light exit.

Figure 4:
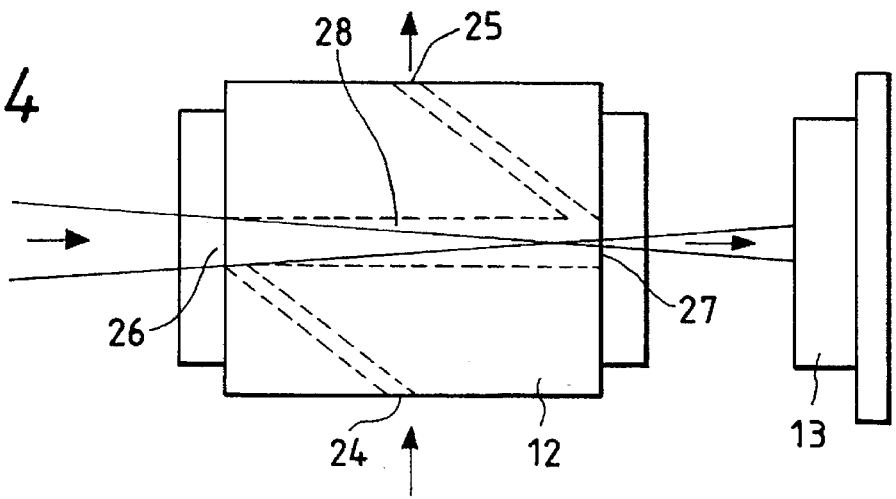
FIG. 4 is a view illustrating a different example and its effect.

FIG. 4 shows a view illustrating an example that a converging position of the light beam is largely deviated toward the light exit from the center of the light transmitting flow path 28 to solve the problem pointed out in FIG. 3.

The example is effective in the case that the optical axis change of the flow cell 12 due to the density change of the liquid flowing in the flow cell 12 is more prominent than the optical axis change of the spectroscope due to the light source position change or temperature change. For a striking change of composition of a liquid in a gradient liquid chromatograph or for a mixture of different liquids in a flow injection analysis and a reaction liquid chromatograph, the measurement error can be reduced by setting the light beam path as shown in FIG. 4 even if components of a sample are dispersed in the light transmitting flow path 28 as in FIG. 3.

Measurement depending on measurement conditions can be accomplished by switching the state in FIG. 2 over the one in FIG. 4. That is, the light is focused at the center of the sample flow path at which quantity of the light entering the flow cell 12 can be made high. If the error cannot be omitted as the optical axis change in the flow cell 12 due to the density change of the liquid flowing the flow cell 12 is too large, the focus should be set to the specimen-side detector 13. This allows the optical system to be set depending on a cause of the measurement error. Switching means include a device for sliding the flow cell 12 toward the light beam and a device for changing a focal length of the light recondensing mirror 10.

As described above, the embodiment can correct at high accuracy the deviation of the optical axis due to intensity of the light source or fluctuation of air in the light source chamber 1. The embodiment also can correct at high accuracy the minute change of the optical axis due to the position deviation or temperature change of the light source that has been insufficient to correct.

The correction can be made without delicate optical adjustment.

The embodiment can converge the light beam around the center of the light transmitting flow path 28 of the flow cell 12 or around the end of the light transmitting flow path 28. This can minimize the quantity of light cut by the inside walls of the flow cell 12.

Such a feature can prevent the light from being decreased. The feature also can remove the unbalancing causes of the sample-side and object-side optical systems so that the change correction accuracy can be increased further.

What is claimed is:

1. An optical detector for a flowing sample, comprising a light source, a spectroscope for dispersing light emitted from the light source, the spectroscope having an exit slit through which the dispersed light is passed, a detector for detecting the light passed through the exit slit, a flow cell positioned in a light path between the detector and the spectroscope, wherein a light condenser for condensing the dispersed light passed through the exit slit are arranged between the spectroscope and the flow cell in the light path, and a distance from the light condenser to the flow cell is shorter than a distance from the exit slit to the light condenser, wherein a demagnified image of the exit slit is formed in the flow cell.

2. The optical detector for a flowing sample according to claim 1 wherein the flow cell and the light condenser are arranged so that the demagnified image is formed at a center of a sample flow path of the flow cell or in a vicinity thereof.

3. The optical detector for a flowing sample according to claim 1 wherein the flow cell is positioned so that a direction of the light path coincides with a sample flowing direction of the flow cell and the flow cell or the light condenser is arranged so that the demagnified image is formed at an end of the flow cell or in the vicinity thereof in the light path direction.

4. The optical detector for a flowing sample according to claim 3 wherein a light beam splitter is arranged between the light condenser to split the light beam into two beams, one of the two beams being detected by the detector through the flow cell and the other of the two beams being detected by another detector.

5. The optical detector for a flowing sample according to claim 4 wherein the light condenser and the flow cell are arranged so that inside walls of the flow cell are substantially prevented from being irradiated with the light therethrough.

6. An optical detector for a flowing sample, comprising a monochromatic light source, a light condenser condensing a monochromatic light beam emitted from the monochromatic light source, a flow cell through which a sample flows, the monochromatic light beam being transmitted through the sample, and a detector detecting the transmitted monochromatic light beam, a distance between the light condenser and the flow cell being shorter than that between the monochromatic light source and the light condenser whereby a demagnified image of the monochromatic light source is formed in the flow cell.

7. An optical detection method for a flowing sample comprising the steps of flowing a sample through a light transmitting flow path, passing light emitted from a light source through a slit, condensing the light passed through the slit by means of a light condenser so as to transmit the light passed through the slit through the light transmitting flow path, and detecting by means of a detector the light passed through the light transmitting flow path, a distance between the light condenser and the light transmitting flow path being shorter than a distance between the slit and the light condenser, whereby a demagnified image of the slit is formed at a predetermined position in the light transmitting flow path.

8. The optical detection method for a flowing sample according to claim 7 wherein a direction of the light transmitting flow path coincides substantially with a direction of the transmitted light.

9. The optical detection method for a flowing sample according to claim 7, further comprising the steps of splitting the light into first and second light beams between the light condenser and the light transmit the first light beam being passed through the light transmitting path to be detected by the detector and the second light beam detected by another detector preventing it from being passed light transmitting flow path, and comparing the detected first and second light beams with each other.

10. The optical detection method for a flowing sample according to claim 7 wherein the predetermined position at which the demagnified image is formed is varied in the light transmitting flow path.

11. The optical detection method for flowing sample according to claim 9 wherein the light from the light source is diffracted before being led to the light transmitting flow path.

12. The optical detection method for flowing sample according to claim 11 wherein the light condenser comprises a concave mirror.

* * * * *